United States Patent [19]

Duer

[11] Patent Number: 5,512,044
[45] Date of Patent: Apr. 30, 1996

[54] EMBOLIC CUTTING CATHETER

[76] Inventor: Edward Y. Duer, No. 31-2 Megamiyama-cho, Koyoen, Nishinomiya 662, Japan

[21] Appl. No.: 320,206

[22] Filed: Oct. 11, 1994

[51] Int. Cl.[6] .................................................. A61B 17/22
[52] U.S. Cl. ............................ 604/22; 606/159; 606/170; 606/180
[58] Field of Search .................................. 606/159, 170, 606/171, 180, 79, 80, 127, 128, 167; 604/22; 128/751, 749

[56] References Cited

U.S. PATENT DOCUMENTS

| | | | |
|---|---|---|---|
| 4,857,046 | 8/1989 | Stevens et al. | 604/22 |
| 4,990,134 | 2/1991 | Auth | 606/22 |
| 4,994,067 | 2/1991 | Summers | 606/159 |
| 5,242,460 | 9/1993 | Klein et al. | 606/159 |
| 5,402,790 | 4/1995 | Jang et al. | 606/159 X |
| 5,403,317 | 4/1995 | Bonutti | 606/80 |

Primary Examiner—Michael H. Thaler
Assistant Examiner—Patrick W. Rasche
Attorney, Agent, or Firm—Roy A. Ekstrand

[57] ABSTRACT

An embolic cutting catheter includes a catheter body having a passage defined therein and supporting an inflatable balloon on the exterior surface thereof. A generally cylindrical housing is received within the interior passage of the catheter body and supports a rotating cutter head assembly having a conical member defining a spiral groove therein. The conical member is secured to a pair of cylindrical members each having spiral grooves defined therein and an abrasive cylindrical surface is positioned between the cylindrical portions. The spiral grooves of the conical member and cylindrical portions cooperate to carry embolic plaque particles into the region of the abrasive cylinder wherein the particles are pulverized and thereafter carried outwardly from the catheter to be disposed of. The conical cutting head defines a rounded apex to avoid injury to the vessel walls of the patient's artery. For added pulverizing capability, the abrasive cylinder is surrounded by an abrasive surface within which the abrasive cylinder rotates.

12 Claims, 2 Drawing Sheets

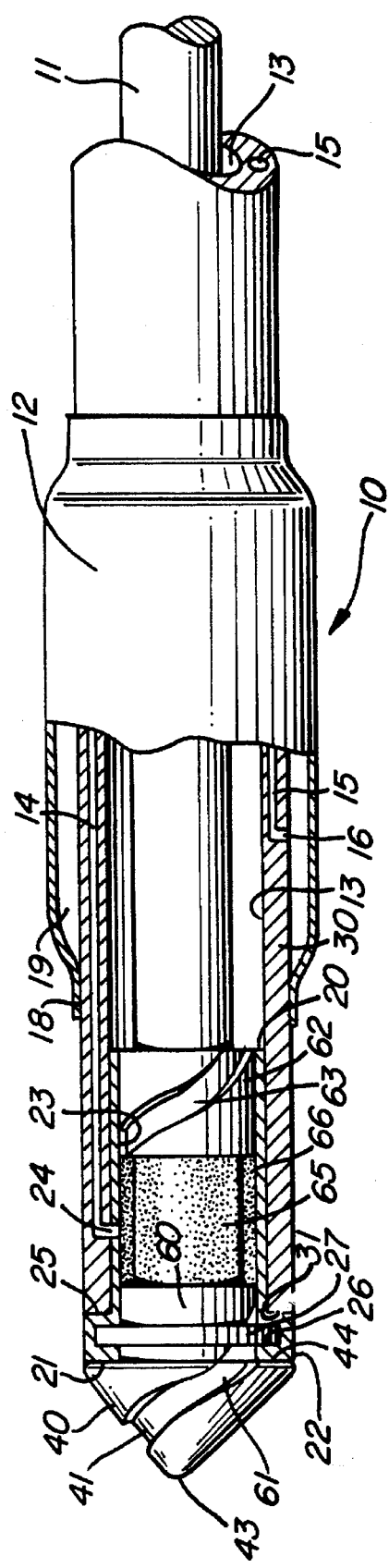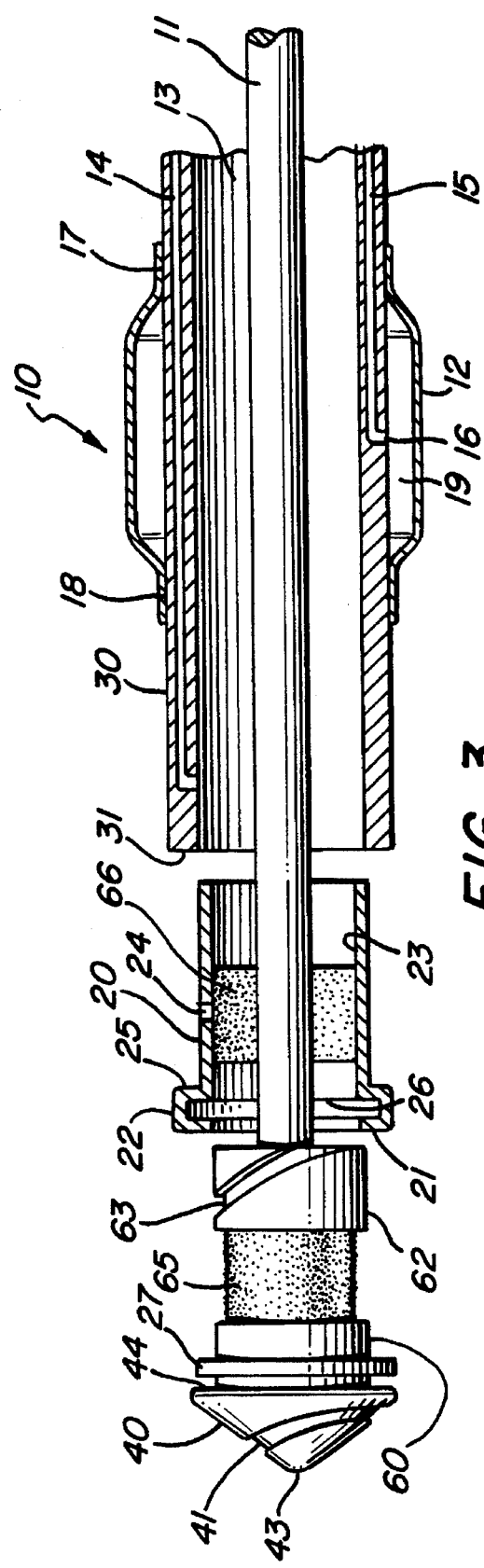

EMBOLIC CUTTING CATHETER

FIELD OF THE INVENTION

This invention relates generally to embolic plaque removal catheters and particularly to apparatus to improve the safety in the use thereof.

BACKGROUND OF THE INVENTION

The accumulation and build-up of plaque or emboli within blood vessel walls presents a very serious problem to humans and other higher order primates. Problems arise in that plaque material attaches itself to the inner walls of blood vessels and begins a process of gradually building-up added plaque whereby the available flow passage within the artery is severely restricted and, if left untreated, leads to blockages of blood flow that lead to serious injury to portions of the heart and other portions of the vascular system. Such blocked or partially blocked arteries usually require serious surgical procedures such as bypass surgery and the like. While a variety of devices have been designed, they most typically comprise a cutting head supported by an elongated usually flexible catheter member which in turn is coupled to a drive mechanism that powers a cutting head inserted into a selected blocked artery via an incision in the outer body and manipulated so as to provide a path for moving the cutting head carefully into the affected area of plaque build-up. The cutting head works to sever the plaque emboli from the inner vessel wall and to loosen and crush it into a fine particle mixture for removal from the blood circulatory system into the liver for elimination. There are several problem areas in the procedure. For example, the use of a sharp cutting tool within the delicate arterial passages expose the patient to substantial risk from damage to the inner walls of the affected artery.

Further, the structures designed to avoid or minimize risk of damage to artery walls presented by the cutter generally rely on some sort of alignment apparatus which itself may tend to block the artery during the treatment which subjects the patient to further risk and potential injury.

The cutter heads of conventional catheters often do not pulverize the plaque debris. This unpulverized plaque debris may actually increase blood flow resistance inside the lumen of the catheter. This problem may persist despite the use of vacuum or negative pressure applied to the catheter from its downstream side. As a result, there arises an increased risk of debris lodging in a downstream segment of the blood vessel which in turn may cause an infarction or blockage.

Thus, while the ability to remove embolic plaque using an inserted cutting tool catheter presents hope for many afflicted individuals, there nonetheless remains a continuing need in the art for evermore effective, improved, less injurious, and safer cutting catheters.

SUMMARY OF THE INVENTION

Accordingly, it is a general object of the present invention to provide an improved emboli cutting catheter for effective arterial plaque removal. It is a more particular object of the present invention to provide an improved emboli cutting catheter which effectively removes arterial plaque without subjecting the patient to obstruction or blocking of the arterial blood flow during the procedure or serious risk of blood vessel injury.

In accordance with the present invention, there is provided an embolic cutting catheter for use in the removal of arterial plaque, the catheter comprises: a catheter body defining an interior passage and a forward end; a cylindrical member having a spiral groove formed therein rotatably supported with respect to the catheter body; a generally conical member defining a spiral groove therein and a circular base, the generally conical member secured to the cylindrical member at the base such that such spiral grooves of the generally conical member and the cylindrical member are aligned to form a continuous spiral path; an abrasive member secured to the cylindrical member; and rotation means for rotating the abrasive member, cylindrical member and the generally conical member.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 2 sets forth a partial section side view of an embolic cutting catheter constructed in accordance with the present invention; and FIG. 3 sets forth a sectioned assembly view of the present invention embolic cutting catheter.

DESCRIPTION OF THE PREFERRED EMBODIMENT

Figure 1:
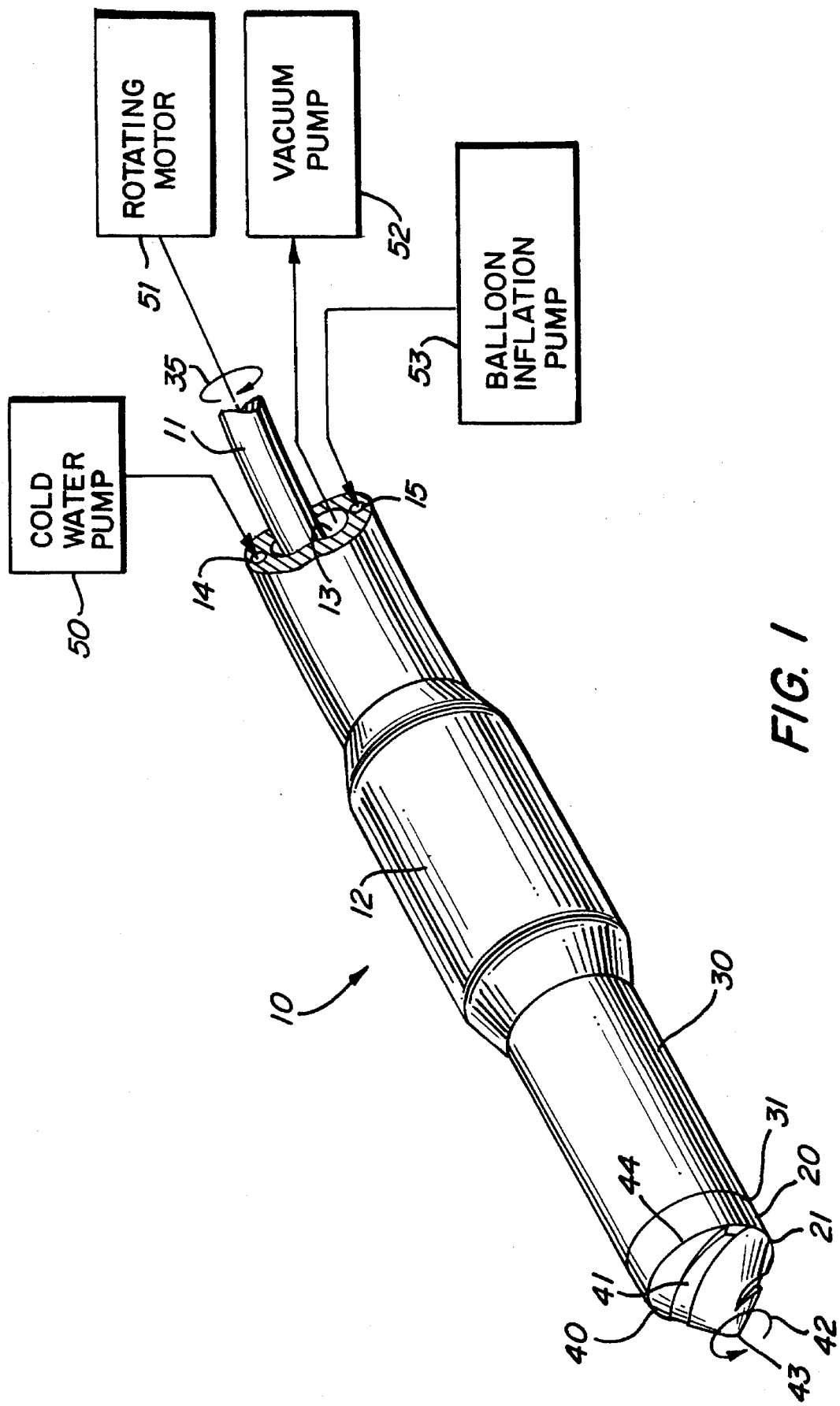
FIG. 1 sets forth a perspective view of an embolic cutting catheter constructed in accordance with present invention.

FIG. 1 sets forth a perspective view of an embolic cutting catheter constructed in accordance with the present invention and generally referenced by numeral 10. Embolic cutting catheter 10 includes a generally cylindrical catheter body 30 having an inflatable balloon 12 sealingly supported thereon. Catheter body 30 is coupled via a passage 13 to a conventional vacuum source 52. Catheter body 30 further defines a lumen 14 coupled to a source of pressurized cold water 50 and a lumen 50 coupled to a source of pressurized liquid 53. Lumen 15 is coupled within catheter body 30 in the manner seen in FIG. 2 to provide inflation of inflatable balloon 12. Catheter body 30 further defines a forward end 31. Embolic cutting catheter 10 further includes a rigid housing 20 received upon and secured to catheter body 30 in the manner described below in greater detail. Rigid body 20 in turn defines a forward end 21. A conical cutting member 40 defines a generally conical shape having a circular base 44 and a rounded apex 43. A spiral or helical groove 41 is formed upon the outer surface of conical member 40 and progresses forwardly from base 44 toward rounded apex 43. Cutting catheter 10 further includes an elongated flexible guide wire 11 extending through catheter body 30 and in the manner described below is coupled to conical member 40. Guide wire 11 is coupled to a source of rotating power 51.

In operation, cutting catheter 10 is inserted through a conveniently located incision in the patient's body and a patient blood vessel and is thereafter moved into the patient's artery or arteries until the desired area of treatment is approached. Rotating motor 51 provides rotation of guide wire 11 in the direction indicated by arrow 35 which in the manner described below in greater detail provides corresponding rotation of conical member 40 in the direction indicated by arrow 42. In accordance with an important aspect of the present invention, the rotation of conical member 40 causes embolic plaque within the patient's artery to be separated and broken down using the drill-like action of conical member 40 and spiral groove 41. As is described below in greater detail, the spiral character of groove 41 causes the particles of embolic plaque to be forced into the interior of rigid housing 20 and catheter body 30 to be further broken down and pulverized by an abrasive cylinder 65 and abrasive surface 66 within catheter body 30 (seen in FIGS. 2 and 3). The operation of conical member 40 and cooperating apparatus within catheter body 30 and rigid housing 20 is described below in greater detail. Suffice it to note here however that as particles are broken down by conical member 40, they are passed through spiral groove 41 to the interior of rigid housing 20 and catheter body 30 for further processing and pulverizing.

Concurrently, the cooperation of vacuum pump 52 and cold water pump 50 produces a water stream and pulverized plaque flow outwardly through passage 13 for disposal. Inflatable balloon 12 may be inflated as desired using a saline solution or the like to provide outward pressure upon the host blood vessel and to provide position stabilizing as well as conventional angioplasty treatment.

FIG. 2 sets forth a partial section view of the present invention embolic cutting catheter. Catheter 10 includes an elongated generally cylindrical catheter body 30 having a water circulation lumen 14 formed therein. Catheter body 30 further defines a forward end 31, an interior passage 13 and a balloon inflation lumen 15 also formed therein. Lumen 15 terminates in an aperture 16. An inflatable balloon 12 is sealingly secured to the outer surface of catheter body 30 by a pair of air-tight seals 17 and 18 and defines an interior cavity 19.

Catheter 10 further includes a generally cylindrical rigid housing 20 defining an interior bore 23 and an aperture 24 received within passage 13 of catheter body 30. Rigid housing 20 further includes a forward end 21 and a shoulder 25 together with a cylindrical outer surface 22. Rigid housing 20 is received and secured within passage 13 of catheter body 30 such that shoulder 5 is secured to forward end 31 of catheter body 30. Outer surface 22 defines an outer diameter substantially equal to the diameter of catheter body 30. In addition, rigid housing 20 defines an annular groove 26 generally centered between shoulder 25 and forward end 21.

Catheter 10 further includes an elongated guide wire 11 extending through passage 13 and having an interior end coupled to a cylindrical guide 62. Cylindrical guide 62 defines a generally cylindrical outer surface having a spiral groove 63 formed therein. The outer diameter of cylindrical guide 62 is sized to fit precisely within bore 23 of rigid housing 20 while permitting turning with respect thereto. Catheter 10 further includes a reduced diameter abrasive cylinder 65 having a cylindrical outer surface which supports an abrasive material such as embedded diamond dust or the like. The diameter of abrasive cylinder 65 is slightly less than that of cylindrical guide 62 providing a clearance between abrasive cylinder 65 and an abrasive surface 66 formed within bore 23 of rigid housing 20. Abrasive surface 66 is generally coincident with the abrasive surface of abrasive cylinder 65 and spaced slightly therefrom. Catheter 10 further includes a cylindrical member 60 having an outer diameter corresponding to cylindrical guide 62 and supporting an annular retainer 27. Cylindrical member 60 further defines a spiral groove 61 and is coupled to a conical member 40. Conical member 40 defines a generally conical shape having a circular base 44 secured to cylindrical member 60 and a rounded apex 43. Conical member 40 further defines a spiral groove 41. In accordance with an important aspect of the present invention, spiral groove 41 of conical member 40 and spiral groove 61 of cylindrical member 60 are aligned such that broken plaque material is able to pass rearwardly through spiral groove 41 and into spiral groove 61 of cylindrical member 60. Cylindrical member 60 is received within bore 23 of rigid housing 20 such that annular retainer 27 is received within groove 26. The capture of retainer 27 within groove 26 secures the combined structure of cylindrical member 60, cylindrical guide 62, abrasive cylinder 65 and conical member 40 within rigid housing 20.

In operation, the present invention catheter is inserted into the target blood vessel with the object of removing calcified embolic plaque which is deposited upon the interior walls of blood vessels. The high speed rotation of guide wire 11 produces a corresponding high speed rotation of the combined assembly formed by conical member 40, cylindrical member 60, abrasive cylinder 65 and cylindrical guide 62. As conical member 50 rotates at high speed, the action of spiral groove 41 upon the embolic plaque severs the embolic plaque from the blood vessel wall and begins breaking down the embolic plaque into a somewhat coarse debris. The spiral character of groove 41 and the direction of rotation of guide wire 11 and conical head 40 cause the particles of embolic plaque to be carried rearwardly through spiral groove 41 and into spiral groove 61 of cylindrical member 60. The annular structure of retainer 27 provides a space between the interior surface thereof and spiral groove 61 permitting the passage of such particles of embolic plaque into the interior of rigid housing 20. The continued rotation of conical member 40 forces the embolic plaque materials into the portion of rigid housing 20 having abrasive surface 66 formed thereon and within which abrasive cylinder 65 is rotating. Also, the portion of catheter 10 between cylindrical member 60 and cylindrical guide 62 receives a flow of pressurized water through aperture 24 formed in rigid housing 20 and lumen 14 formed in catheter body 30. The rotation of abrasive cylinder 65 causes the pulverization of embolic plaque particles which then flows rearwardly to be introduced into spiral groove 63 of cylindrical guide 62. The direction of rotation of cylindrical guide 62 and spiral groove 63 causes the pulverized plaque material to be carried outwardly through spiral groove 63 and into passage 13 of catheter body 30. The combination of water flow and pulverized plaque particles then passes outwardly through passage 13 under the urging of the negative pressure or partial vacuum applied thereto.

In accordance with an important aspect of the present invention, the conical shape and rounded apex of conical member 40 avoids injury or damage to the patient's blood vessel walls while spiral groove 41 provides effective attack of embolic plaque within the blood vessel. Because of the thorough pulverizing action of abrasive cylinder 65 and abrasive surface 66, the pulverized plaque debris is extremely fine having particle diameters in the micron range. As a result, the flow resistance of the pulverized debris in the patient's bloodstream is quite low and will flow smoothly through the fine catheter lumen and be expelled outside the body.

While it will be apparent to those skilled in the art that the present invention embolic cutting catheter may be fabricated of a variety of materials, it has been found advantageous to fabricate conical member 40, cylindrical member 60, abrasive cylinder 65, and cylindrical guide 62 together with rigid housing 20 of a titanium alloy, stainless steel or a blood-compatible hard plastic such as polycarbonate or the like. While it will recognized that a variety of abrasive materials may be used to form abrasive cylinder 65 and abrasive surface 66, it has been found particularly advantageous to utilize a diamond dust abrasive embedded in the surfaces of cylinder 65 and surface 66. Guide wire 11 may be fabricated of a variety of resilient strong materials such as stainless steel or the like. To prevent damage to the interior walls of the catheter subjected to the rotation of guide wire 11, guide 11 may be coated with a pliable plastic material. Catheter body 30 is preferably formed of a material having superior blood compatibility, as for example, titanium alloy, stainless steel, or a hard plastic material such as polycarbonate. Balloon 12 is preferably fabricated of a plastic material having good blood capability such as polyvinyl chloride, nylon, polyurethane, Teflon, or polyethylene terephthalate.

It has been recognized in the operation of the present invention embolic cutting catheter that the production of heat due to friction between the rotating head components and the housing components may be minimized by utilizing a silicon oil having good blood compatibility applied to the contacting surfaces of each component. Alternatively, a separate cold water cooling feed lumen may be utilized which is not shown in the accompanying drawings.

FIG. 3 sets forth a sectioned assembly view of the present invention embolic cutting catheter. Catheter 10 includes an elongated generally cylindrical catheter body 30 having a water circulation lumen 14 formed therein. Catheter body 30 further defines a forward end 31, an interior passage 13 and a balloon inflation lumen 15 also formed therein. Lumen 15 terminates in an aperture 16. An inflatable balloon 12 is sealingly secured to the outer surface of catheter body 30 by a pair of air-tight seals 17 and 18 and defines an interior cavity 19.

Catheter 10 further includes a generally cylindrical rigid housing 20 defining an interior bore 23 and an aperture 24 received within passage 13 of catheter body 30. Rigid housing 20 further includes a forward end 21 and a shoulder 25 together with a cylindrical outer surface 22. Rigid housing 20 is received and secured within passage 13 of catheter body 30 such that shoulder 25 is secured to forward end 31 of catheter body 30. Outer surface 22 defines an outer diameter substantially equal to the diameter of catheter body 30. In addition, rigid housing 20 defines an annular groove 26 generally centered between shoulder 25 and forward end 21.

Catheter 10 further includes an elongated guide wire 11 extending through passage 13 and having an interior end coupled to a cylindrical guide 62. Cylindrical guide 62 defines a generally cylindrical outer surface having a spiral groove 63 formed therein. The outer diameter of cylindrical guide 62 is sized to fit precisely within bore 23 of rigid housing 20 while permitting turning with respect thereto. Catheter 10 further includes a reduced diameter abrasive cylinder 65 having a cylindrical outer surface which supports an abrasive material such as embedded diamond dust or the like. The diameter of abrasive cylinder 65 is slightly less than that of cylindrical guide 62 providing a clearance between abrasive cylinder 65 and an abrasive surface 66 formed within bore 23 of rigid housing 20. Abrasive surface 66 is generally coincident with the abrasive surface of abrasive cylinder 65 and spaced slightly therefrom. Catheter 10 further includes a cylindrical member 60 having an outer diameter corresponding to cylindrical guide 62 and supporting an annular retainer 27. Cylindrical member 60 further defines a spiral groove 61 and is coupled to a conical member 40. Conical member 40 defines a generally conical shape having a circular base 44 secured to cylindrical member 60 and a rounded apex 43. Conical member 40 further defines a spiral groove 41. In accordance with an important aspect of the present invention, spiral groove 41 of conical member 40 and spiral groove 61 of cylindrical member 60 are aligned such that broken plaque material is able to pass rearwardly through spiral groove 41 and into spiral groove 61 of cylindrical member 60. Cylindrical member 60 is received within bore 23 of rigid housing 20 such that annular retainer 27 is received within groove 26. The capture of retainer 27 within groove 26 secures the combined structure of cylindrical member 60, cylindrical guide 62, abrasive cylinder 65 and conical member 40 within rigid housing 20.

In the assembly of the present invention catheter, retainer 27 may comprise a spring-like split washer which may be compressed upon cylindrical member 60 and inserted into bore 23 until the retainer is aligned with groove 26. Thereafter, retainer 27 expands outwardly and is secured within groove 26. The combined structure is then assembled within passage 13 of catheter body 30 and secured using conventional attachment means. Alternatively, rigid housing 20 may be fabricated as a split housing which is assembled about the combined structure of cylindrical member 60, cylindrical guide 62, retainer 27 and abrasive cylinder 65 by joining the split housing parts and seating retainer 27 within groove 26. Thereafter, the mated split housing of rigid housing 20 together with the inserted components therein may be assembled within passage 13 of catheter body 30 and secured therein using conventional fabrication means. In either event, the resulting structure provides a compact, highly efficient and safe embolic cutting catheter.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. An embolic cutting catheter for use in the removal of arterial plaque, said catheter comprising:

a catheter body defining an interior passage and a forward end;

a rotatable cutter head assembly having, a generally conical member defining a base, a rounded apex and a first spiral groove therebetween, a cylindrical member secured to said base and defining a second spiral groove therein, an abrasive cylinder secured to said cylindrical member having an abrasive outer surface, a cylindrical guide secured to said abrasive cylinder and defining a third spiral groove therein; and a guide wire extending through said interior passage of said catheter body and having a forward end secured to said cylindrical guide, said cylindrical member, said abrasive cylinder, said cylindrical guide and said guide wire being rotatably supported within said catheter body interior passage such that said generally conical member is supported at said base proximate said forward end of said catheter body.

2. An embolic cutting catheter as set forth in claim 1 further including a rigid housing defining a bore therein received within said interior passage of said catheter body, said cylindrical member, said abrasive and said cylindrical guide being received within said bore in a rotatable support.

3. An embolic cutting catheter as set forth in claim 2 wherein said rigid housing defines an abrasive surface formed on said bore overlying at least a portion of said abrasive cylinder.

4. An embolic cutting catheter as set forth in claim 3 wherein said rigid housing defines an annular groove and wherein said cylindrical member includes an annular retainer extending into said groove.

5. An embolic cutting catheter as set forth in claim 4 wherein said catheter body includes an inflatable external balloon.

6. An embolic cutting catheter as set forth in claim 5 wherein said catheter body defines a lumen passage having an output aperture for passing water through said aperture and wherein said rigid housing defines an aperture aligned with said output aperture for passing said water to said abrasive cylinder, said water flowing between said abrasive cylinder and said abrasive surface and through said third spiral groove and outwardly through said interior passage.

7. An embolic cutting catheter comprising:
- a catheter body having an interior passage and a forward end;
- a cutter head assembly having a pair of spaced apart cylindrical members, an abrasive cylinder therebetween rotatably supported within said interior passage and a tapered cutter secured to one of said cylindrical members proximate said forward end, said tapered cutter and said spaced apart cylindrical members defining exterior spiral grooves; and
- a flexible guide wire extending into said interior passage and having an interior end secured to the innermost of said cylindrical member.

8. An embolic cutting catheter as set forth in claim 7 further including a rigid generally cylindrical housing inserted into said interior passage at said forward end, said rigid generally cylindrical housing defining an internal bore receiving said pair of cylindrical members and said abrasive cylinder.

9. An embolic cutting catheter as set forth in claim 8 wherein said rigid generally cylindrical housing defines an abrasive surface within said internal bore overlying at least a portion of said abrasive cylinder.

10. An embolic cutting catheter as set forth in claim 9 wherein said tapered cutter is generally conical and defines a rounded apex.

11. An embolic cutting catheter as set forth in claim 10 further including a rigid generally cylindrical housing inserted into said interior passage at said forward end, said rigid generally cylindrical housing defining an internal bore receiving said pair of cylindrical members and said abrasive cylinder.

12. An embolic cutting catheter as set forth in claim 11 wherein said rigid generally cylindrical housing defines an abrasive surface within said internal bore overlying at least a portion of said abrasive cylinder.

\* \* \* \* \*